United States Patent
Tomioka et al.

[11] Patent Number: 5,252,590
[45] Date of Patent: * Oct. 12, 1993

[54] 1-PYRIDYLIMIDAZOLE DERIVATIVE

[75] Inventors: Hiroki Tomioka, Tokyo; Noriyasu Sakamoto, Nishinomiya; Kimitoshi Umeda; Hiroaki Fujimoto, both of Toyonaka; Takao Ishiwatari, Minoo; Hirosi Kisida, Takarazuka, all of Japan

[73] Assignee: Sumitomo Chemical Company, Limited, Osaka, Japan

[*] Notice: The portion of the term of this patent subsequent to Jun. 16, 2009 has been disclaimed.

[21] Appl. No.: 903,135

[22] Filed: Jun. 24, 1992

[30] Foreign Application Priority Data

Jun. 28, 1991 [JP] Japan .................. 3-185735

[51] Int. Cl.⁵ .................. A61K 31/44; C07D 401/04
[52] U.S. Cl. .................. 514/341; 546/278
[58] Field of Search .................. 546/278; 514/341

[56] References Cited

U.S. PATENT DOCUMENTS

| | | | |
|---|---|---|---|
| 3,868,458 | 2/1975 | Baker et al. | 514/399 |
| 3,940,484 | 2/1976 | Baker et al. | 514/235 |
| 3,996,366 | 12/1976 | Baker et al. | 514/399 |
| 4,048,188 | 9/1977 | Baker et al. | 548/341 |
| 4,786,312 | 11/1988 | Schmierer et al. | 548/343 |
| 4,987,146 | 1/1991 | Rohde et al. | 514/397 |
| 5,043,454 | 8/1991 | Wriede et al. | 548/337 |
| 5,122,530 | 6/1992 | Tomioka et al. | 514/341 |

FOREIGN PATENT DOCUMENTS

| | | |
|---|---|---|
| 0200299 | 11/1985 | European Pat. Off. |
| 0270091 | 6/1988 | European Pat. Off. |
| 0358595 | 3/1990 | European Pat. Off. |
| 0385084 | 9/1990 | European Pat. Off. |
| 0396427 | 11/1990 | European Pat. Off. |
| 0445931 | 9/1991 | European Pat. Off. |
| 0464979 | 1/1992 | European Pat. Off. |

OTHER PUBLICATIONS

Tomioka et al., CA 116: 128919n, 1992 and CA 116 (15): 151765t, 1992.

*Primary Examiner*—Jane T. Fan
*Attorney, Agent, or Firm*—Stevens, Davis, Miller & Mosher

[57] ABSTRACT

A novel pyridylimidazole derivative having the formula;

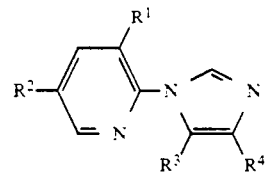

wherein $R^1$ is a halogen atom, a nitro group or a trifluoromethyl group; $R^2$ is a $C_1$-$C_3$ haloalkyl group or a $C_1$-$C_3$ haloalkoxy group; $R^3$ is a $C_1$-$C_3$ alkyl group; $R^4$ is a tert-butyl group or a $C_1$-$C_4$ haloalkyl group, a process for producing the same and insecticides containing the same as an active ingredient, are disclosed.

9 Claims, No Drawings

1-PYRIDYLIMIDAZOLE DERIVATIVE

BACKGROUND OF THE INVENTION

1. Field of the Invention

The present invention relates to a novel pyridylimidazole derivative having the formula (I):

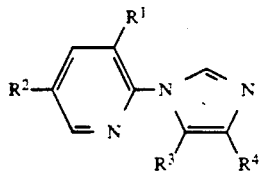

wherein $R^1$ is a halogen atom, a nitro group or a trifluoromethyl group; $R^2$ is a $C_1$-$C_3$ haloalkyl group or a $C_1$-$C_3$ haloalkoxy group; $R^3$ is a $C_1$-$C_3$ alkyl group; $R^4$ is a tert-butyl group or a $C_1$-$C_4$ haloalkyl group, a process for producing the same and insecticides containing the same as an active ingredient.

2. Description of the Related Art

It is described in U.S. Pat. No. 3,868,458, U.S. Pat. No. 3,940,484 and U.S. Pat. No. 3,996,366 that a certain imidazole derivative is useful as an active ingredient of insecticide.

As a result of extensive investigations on compounds having an excellent insecticidal effect, the present inventors have found a pyridylimidazole derivative having the formula (I) exhibit an extremely high insecticidal effect, and thus have accomplished the present invention.

SUMMARY OF THE INVENTION

According to the present invention, there is provided a pyridylimidazole derivative having the formula (I):

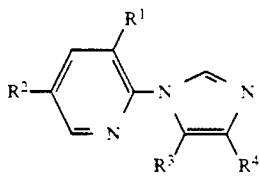

wherein $R^1$ is a halogen atom, a nitro group or a trifluoromethyl group; $R^2$ is a $C_1$-$C_3$ haloalkyl group or a $C_1$-$C_3$ haloalkoxy group; $R^3$ is a $C_1$-$C_3$ alkyl group; $R^4$ is a tert-butyl group or a $C_1$-$C_4$ haloalkyl group, a process for producing the same and insecticides containing the same as an active ingredient.

DESCRIPTION OF THE PREFERRED EMBODIMENTS

Hereinafter, the present invention is explained in detail.

In the pyridylimidazole derivative (I), examples of a halogen atom are a fluorine atom, a chlorine atom, a bromine atom and an iodine atom. Examples of a $C_1$-$C_3$ haloalkyl group represented by $R^2$ are a trifluoromethyl group, a pentafluoroethyl group and a heptafluoropropyl group, etc.

Examples of a $C_1$-$C_3$ haloalkoxy group represented by $R^2$ are a trifluoromethoxy group, a difluoromethoxy group, and a tetrafluoroethoxy group, etc. Examples of a $C_1$-$C_3$ alkyl group represented by $R^3$ are a methyl group, an ethyl group, a propyl group and isopropyl group. Examples of a $C_1$-$C_4$ haloalkyl group represented by $R^4$ are a trifluoromethyl group, a pentafluoroethyl group, 2-chloro-1,1,2,2,-tetrafluoroethyl group, 2-bromo-1,1,2,2-tetrafluoroethyl group, 1,1,2,2-tetrafluoroethyl group, a heptafluoropropyl group and nonafluorobutyl group, etc.

Among the pyridylimidazole derivative (I), preferred are those wherein $R^1$ is a fluorine atom, a chlorine atom or a nitro group; $R^2$ is a $C_1$-$C_3$ haloalkyl group which comprises at least a fluorine atom; $R^3$ is a $C_1$-$C_3$ alkyl group; $R^4$ is a tert-butyl group or a $C_1$-$C_3$ haloalkyl group which comprises at least a fluorine atom, a chlorine atom or a bromine atom as the halogen atom.

More preferred are those wherein $R^1$ is a fluorine atom or a chlorine atom; $R^2$ is a trifluoromethyl group; $R^3$ is a methyl group; $R^4$ is a $C_1$-$C_3$ haloalkyl group which comprises at least a fluorine atom, a chlorine atom or a bromine atom as the halogen atom.

Most preferred are those wherein $R^1$ is a chlorine atom; $R^2$ is a trifluoromethyl group; $R^3$ is a methyl group; $R^4$ is a haloalkyl group represented by the formula, $-CF_2CF_2X$, in which X is a hydrogen atom, a fluorine atom, a chlorine atom or a bromine atom.

The pyridylimidazole derivative (I) can be produced according to the following reaction scheme.

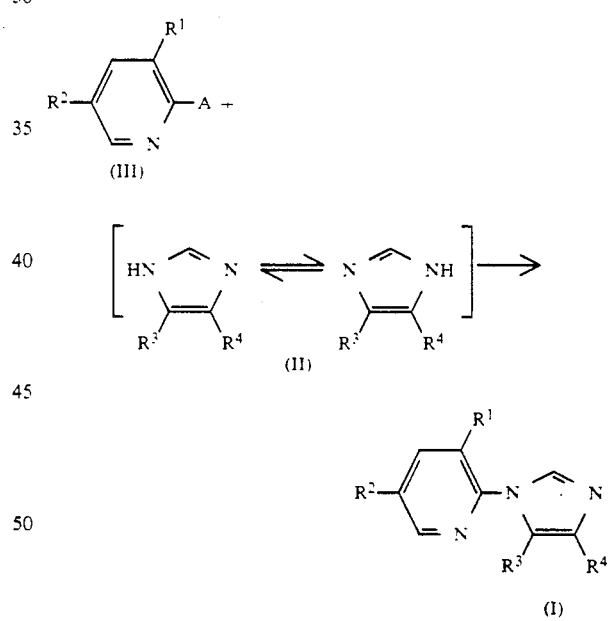

wherein $R^1$, $R^2$, $R^3$ and $R^4$ are each as defined above and A is a halogen atom.

The pyridylimidazole derivative (I) can be produced by reacting the halide compound having the formula:

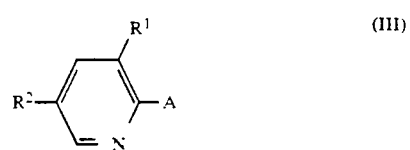

wherein $R^1$, $R^2$ and A are each as defined above with the imidazole derivative having the formula:

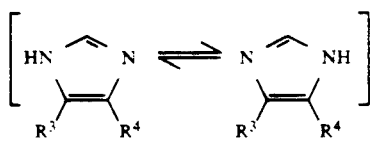

wherein $R^3$ and $R^4$ are each as defined above at from about $-5°$ C. to about 150° C. for about from 1 to 24 hours in an inert solvent in the presence of a reagent for removing a hydrogen halide.

The molar proportion of the halide compound (III) and the imidazole derivative (II) to be used for the reaction is not limitative but is ordinary to be from 1 to 1:2.

The amount of the reagent for removing a hydrogen halide is not also limitative but it is preferably to be from one to four equivalents.

Examples of the inert solvent are aliphatic hydrocarbons (e.g. hexane, heptane, ligroin, petroleum ether, etc.); aromatic hydrocarbons (e.g. benzene, toluene, xylene, etc.); halogenated hydrocarbons (e.g. chloroform, carbon tetrachloride, dichloroethane, chlorobenzene, dichlorobenzene, etc.); ethers (e.g. diethyl ether, diisopropyl ether, dioxane, tetrahydrofuran, ethylene glycol dimethyl ether, etc.); ketones (e.g. acetone, methyl ethyl ketone, methyl isobutyl ketone, isophorone, cyclohexanone, etc.); esters (e.g. ethyl acetate, butyl acetate, etc.); nitro compounds (e.g. nitroethane, nitrobenzene, etc.); nitriles (e.g. acetonitrile, isobutyronitrile, etc.); tertiary amines (e.g. pyridine, triethylamine, N,N-diethylaniline, tributylamine, N-methylmorpholine, etc.); acid amides (e.g. formamide, N,N-dimethylformamide, N,N-dimethylacetamide, etc.); sulfur compounds (e.g. dimethylsulfoxide, sulfolane, etc.); or mixtures thereof.

Examples of the reagent of removing hydrogen halide are organic bases (e.g. pyridine, triethylamine, N,N-diethylaniline, etc.); inorganic bases (e.g. sodium hydroxide, potassium hydroxide, sodium carbonate, potassium carbonate, sodium hydrogen carbonate, calcium carbonate, sodium hydride, etc.); alkali metal alkoxides such as sodium methoxide, sodium ethoxide, etc.).

After completion of the reaction, post-treatment follows in a conventional manner. If necessary and desired, the product may further be purified by chromatography, distillation, recrystallization, etc.

Among the starting compounds in the above processes, the imedazole derivative (II) and the halide compound (III) are prepared by the methods described in U.S. Pat. No. 3,868,458, U.S. Pat. No. 3,940,484, U.S. Pat. No. 3,996,366, J. Org. Chem., 47, 2867 (1982), Japan Patent (laid open) 86-286,370 and U.S. Pat. No. 3,888,932, U.S. Pat. No. 3,928,416, European Patent 23,100, European Patent 34,402, West German patent 2,606,393, West German Patent 3,545,570, U.S. Pat. No. 4,184,041, British Patent 2,002,368, British Patent 1,121,211, Japan Patent (laid open) 84-20,269 respectively, or in a manner similar to the methods.

Examples of the pyridylimidazole derivatives (I) are shown in Table 1 below.

TABLE 1

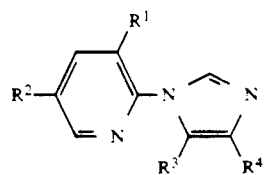

| $R^1$ | $R^2$ | $R^3$ | $R^4$ |
| --- | --- | --- | --- |
| Cl | $CF_3$ | $CH_3$ | $CF_3$ |
| Cl | $CF_3$ | $CH_3$ | $CF_2CF_3$ |
| Cl | $CF_3$ | $CH_3$ | $CF_2CF_2CF_3$ |
| Cl | $CF_3$ | $CH_3$ | $(CF_2)_3CF_3$ |
| Cl | $CF_3$ | $CH_3$ | $CF_2CF_2Br$ |
| Cl | $CF_3$ | $CH_3$ | $CF_2CF_2Cl$ |
| Cl | $CF_3$ | $CH_3$ | $CF_2CF_2H$ |
| Cl | $CF_3$ | $CH_3$ | tert-$C_4H_9$ |
| $CF_3$ | $CF_3$ | $CH_3$ | $CF_3$ |
| $CF_3$ | $CF_3$ | $CH_3$ | $CF_2CF_3$ |
| $CF_3$ | $CF_3$ | $CH_3$ | $CF_2CF_2CF_3$ |
| $CF_3$ | $CF_3$ | $CH_3$ | $(CF_2)_3CF_3$ |
| $CF_3$ | $CF_3$ | $CH_3$ | $CF_2CF_2Br$ |
| $CF_3$ | $CF_3$ | $CH_3$ | $CF_2CF_2Cl$ |
| $CF_3$ | $CF_3$ | $CH_3$ | $CF_2CF_2H$ |
| $CF_3$ | $CF_3$ | $CH_3$ | tert-$C_4H_9$ |
| Cl | $OCHF_2$ | $CH_3$ | $CF_2CF_3$ |
| Cl | $OCHF_2$ | $CH_3$ | $CF_2CF_2Br$ |
| Cl | $OCHF_2$ | $CH_3$ | $CF_2CF_2Cl$ |
| Cl | $OCHF_2$ | $CH_3$ | $CF_2CF_2H$ |
| Cl | $OCClF_2$ | $CH_3$ | $CF_2CF_3$ |
| Cl | $OCClF_2$ | $CH_3$ | $CF_2CF_2Br$ |
| Cl | $OCClF_2$ | $CH_3$ | $CF_2CF_2Cl$ |
| Cl | $OCClF_2$ | $CH_3$ | $CF_2CF_2H$ |
| Cl | $CF_3$ | $CH_2CH_3$ | $CF_3$ |
| Cl | $CF_3$ | $CH_2CH_3$ | $CF_2CF_3$ |
| Cl | $CF_3$ | $CH_2CH_3$ | $CF_2CF_2CF_3$ |
| Cl | $CF_3$ | $CH_2CH_3$ | $CF_2CF_2Br$ |
| Cl | $CF_3$ | $CH_2CH_3$ | $CF_2CF_2Cl$ |
| Cl | $CF_3$ | $CH_2CH_3$ | $CF_2CF_2H$ |
| Cl | $CF_3$ | $CH_2CH_3$ | tert-$C_4H_9$ |
| $CF_3$ | $CF_3$ | $CH_2CH_3$ | $CF_3$ |
| $CF_3$ | $CF_3$ | $CH_2CH_3$ | $CF_2CF_3$ |
| $CF_3$ | $CF_3$ | $CH_2CH_3$ | $CF_2CF_2CF_3$ |
| $CF_3$ | $CF_3$ | $CH_2CH_3$ | $CF_2CF_2Br$ |
| $CF_3$ | $CF_3$ | $CH_2CH_3$ | $CF_2CF_2Cl$ |
| $CF_3$ | $CF_3$ | $CH_2CH_3$ | $CF_2CF_2H$ |
| $CF_3$ | $CF_3$ | $CH_2CH_3$ | tert-$C_4H_9$ |
| Cl | $CF_3$ | $CH_2CH_2CH_3$ | $CF_3$ |
| Cl | $CF_3$ | $CH_2CH_2CH_3$ | $CF_2CF_3$ |
| Cl | $CF_3$ | $CH_2CH_2CH_3$ | $CF_2CF_2CF_3$ |
| Cl | $CF_3$ | $CH_2CH_2CH_3$ | $CF_2CF_2Br$ |
| Cl | $CF_3$ | $CH_2CH_2CH_3$ | $CF_2CF_2Cl$ |
| Cl | $CF_3$ | $CH_2CH_2CH_3$ | $CF_2CF_2H$ |
| Cl | $CF_3$ | $CH_2CH_2CH_3$ | tert-$C_4H_9$ |
| $CF_3$ | $CF_3$ | $CH_2CH_2CH_3$ | $CF_3$ |
| $CF_3$ | $CF_3$ | $CH_2CH_2CH_3$ | $CF_2CF_3$ |
| $CF_3$ | $CF_3$ | $CH_2CH_2CH_3$ | $CF_2CF_2CF_3$ |
| $CF_3$ | $CF_3$ | $CH_2CH_2CH_3$ | $CF_2CF_2Br$ |
| $CF_3$ | $CF_3$ | $CH_2CH_2CH_3$ | $CF_2CF_2Cl$ |
| $CF_3$ | $CF_3$ | $CH_2CH_2CH_3$ | $CF_2CF_2H$ |
| $CF_3$ | $CF_3$ | $CH_2CH_2CH_3$ | tert-$C_4H_9$ |
| $CF_3$ | $CF_3$ | $CH_2CH_3$ | $(CF_2)_3CF_3$ |
| Cl | $CF_3$ | $CH_2CH_3$ | $(CF_2)_3CF_3$ |
| Cl | $CF_3$ | $CH_2CH_2$ | $(CF_2)_3CF_3$ |
| $CF_3$ | $CF_3$ | $CH_2CH_3$ | $(CF_2)_3CF_3$ |

Examples of harmful insects against which the pyridylimidazole derivatives (I) exhibit controlling effects are shown below.

Harmful insects belonging to Hemiptera

Planthoppers such as small brown planthopper (*Laodelphax striatellus*), brown planthopper (*Nilaparvata lugens*), white-backed rice planthopper (*sogatella furcifera*), etc.; leafhoppers such as green rice leafhopper (*Nephotettix cinticeps*), (*Nephotettix virescens*), etc.; aphids, bugs, whiteflies, scales, lace bugs, psyllids, etc.

Lepidoptera

Pyralid moths such as rice stem borer (*Chilo suppressalis*), rice leafroller (*Cnaphalocrocis medinalis*), Indian meal moth (*Plodia interpunctella*), etc.; moths such as tobacco cutworm (*Spodoptera litura*), rice armyworm (*Pseudaletia separata*), cabbage armyworm (*Mamestra brassicae*), etc.; Pieridae such as common cabbageworm (*Pieris rapae crucivora*), etc.; Tortricidae or tortricid moths such as *Adoxophyes* spp., *Grapholita* spp., etc.; Carposinidae, lyonetiid moths (Lyonetiidae), tussock moths (Lymantriidae), beet semi-looper (*Autographa nigrisigna*); harmful insects belonging to *Agrothis* spp. such as turnip cutworm (*Agrothis segetum*), black cutworm (*Agrothis ipsilon*); harmful insects belonging to *Hiliothis* spp.; diamondback moth (*Plutella xylostella*), clothes moths (*Tinedidae*), casemaking clothes moth (*Tinea translucens*), webbing clothes moth (*Tineola biselliella*); etc.

Harmful insects belonging to Diptera

Mosquitos such as common mosquito (*Culex pipiens pallens*), *Culex tritaeniorhynchus*, etc.; *Aedes* spp. such as *Aedes aegypti*, *Aedes albopictus*, etc.; *Anopheles* spp. such as *Anopheles sinensis*, etc.; midges (Chironmoidae); Muscidae such as housefly (*Musca domestica*), false stablefly (*Muscina stabulans*), etc.; Calliphoridae; Sarcophagidae; lesser housefly (*Fannia canicularis*); Anthomyiidae or anthomyiid flies such as seedcorn maggot (*Delia platura*), onion maggot (*Delia antigua*), etc.; fruit flies (Tephritidae); small fruit flies (Drosophilidae); moth flies (Psychodidae); black flies (Simuliidae); Tabanidae; stable flies (Stomoxyidae); etc.

Harmful insects belonging to Coleoptera

Corn root worms such as western corn rootworm (*Diabrotica virgifera*), southern corn root worm (*Diabrotica undecimpunctata*), etc.; scarabs (Scarabaeidae) such as cupreous chafer (*Anomala cuprea*), soybean beetle (*Anomala rufocuprea*), etc.; weevils such as maize weevil (*Sitophilus zeamais*), rice water weevil (*Lissorhoptrus oryzophilus*), adzuki been weevil (*Calosobruchys chineneis*), etc.; darkling beetles (Tenebrionidae) such as yellow mealworm (*Tenebrio molitor*), red fluor beetle (*Tribolium castaneum*), etc.; leaf beetles (Chrysomelidae) such as cucurbit leaf beetle (*Aulacophora femoralis*), striped flea beetles (*Phyllotreta striolata*), etc.; Anobiidae; *Epilachna* spp. such as twenty-eight-spotted ladybirds (*Epilachna vigintioctopunctata*), etc.; powderpost beetles (Lyctidae); false powderpost beetles (Bostrychidae), Cerambycidae; robe beetle (*Paederus fusipes*), etc.

Harmful insects belonging to Dictyoptera

German cockroach (*Blattella germanica*), smoky-brown cockroach (*Periplaneta fuliginosa*), American cockroach (*Periplaneta americana*), brown cockroach (*Periplaneta brunnea*), oriental cockroach (*Blatta orientalis*), etc.

Harmful insects belonging to Thysanoptera

*Thrips palmi*, flower thrips (*Thrips hawaiiensis*), etc.

Harmful insects belonging to Hymenoptera ants (Formicidae); hornets (Vespidae); bethylid wasps (Bethylidae); sawflies (Tenthredinidae) sch as cabbage sawfly (*Athalia rosae ruficornis*), etc.

Harmful insects belonging to Orthoptera mole crickets (Gryllotalpidae); grasshoppers (Acrididae), etc.;

Harmful insects belonging to Aphaniptera

*Purex irritans*, etc.

Harmful insects belonging to Anoplura

*Pediculus humanus capitis*, *Phthirus pubis*, etc.

Harmful insects belonging to Isoptera

*Reticulitermes speratus*, Formosan subterranean termite (*Coptotermes formosanus*), etc.

Moreover, the pyridylimidazole derivatives (I) are very effective to the insects which develop the resistance against conventional insecticides.

In the case that the pyridylimidazole derivatives (I) are used as the active ingredient of insecticidal compositions, the pyridylimidazole derivatives (I) may be used as they are, without adding any other components but in general, the pyridylimidazole derivatives (I) are mixed with a solid carrier, a liquid carrier, a gaseous carrier, a feed, etc. and, if necessary and desired, the mixture is further supplemented with a surfactant and other adjuvants used to prepare insecticidal preparations and prepared into forms such as oil sprays, emulsifiable concentrates, wettable powders, flowable concentrated, granules, dusts, aerosol, fumigants (fogging, etc.), poison bait, etc.

These formulations contain generally 0.01 to 95% by weight of the pyridylimidazole derivatives (I) as the active ingredient.

Examples of the solid carrier used for making formulations are fine powders or granulates, etc. of clays (e.g. kaolin clay, diatomaceous earth, synthetic hydrated silicon dioxide, bentonite, Fubasami clay terra alba, etc.), talc, ceramics, other inorganic minerals (e.g. sericite, quartz, sulfur, activated carbon, calcium carbonate, hydrated silica, etc.), chemical fertilizers (e.g. ammonium sulfate, ammonium phosphate, ammonium nitrate, urea, ammonium chloride, etc.), etc. Examples of the liquid carrier are water, alcohols (e.g. methanol, ethanol, etc.), ketones (e.g. acetone, methyl ethyl ketone, etc.), aromatic hydrocarbons (e.g. benzene, toluene, xylene, ethylbenzene, methylnaphthalene, etc.), aliphatic hydrocarbons (e.g. hexane, cyclohexane, kerosene, gas oil, etc.), esters (e.g. ethyl acetate, butyl acetate, etc.), nitriles (e.g. acetonitrile, isobutyronitrile, etc.), ethers (e.g. diisopropyl ether, dioxan, etc.), acid amides (e.g. N,N-dimethylformamide, N,N-dimethylacetamide, etc.), halogenated hydrocarbons (e.g. dichloromethane, trichloroethane, carbon tetrachloride, etc.), dimethylsulfoxide; vegetable oils such as soybean oil, cotton seed oil, etc. Examples of the gaseous carrier, i.e., propellant, are freon gas, butane gas, LPG (e.g. liquefied petroleum gas), dimethyl ether, carbon dioxide, etc.

Examples of the surfactant are alkyl sulfates, alkyl sulfonic acid salts, alkylaryl sulfonic acid salts, alkyl aryl ethers and polyoxyethylene derivatives thereof, polyethylene glycol ether, polyvalent alcohol esters, sugar alcohol derivatives, etc.

Examples of the adjuvants such as binders, dispersing agents, etc. for formulations are casein, gelatin, polysaccharides (e.g. starch powders, gum arabic, cellulose derivatives, alginic acid, etc.), lignin derivatives, bentonite, sugars, synthetic water-soluble high molecular substances (e.g. polyvinyl alcohol, polyvinylpyrrolidone, polyacrylic acid, etc.). Examples of the stabilizer include PAP (e.g. acidic isopropyl phosphate), BHT (e.g. 2,6-di-tert-butyl-4-methylphenol), BHA (e.g. mixture of 2-tert-butyl-4-methoxyphenol and 3-tert-butyl-4-methoxyphenol), vegetable oils, mineral oils, surfactants, fatty acids or esters thereof, and the like.

As a base material for the poison baits, there are, for example, feed components (e.g. crop powders, essential vegetable oil, sugars, crystalline cellulose etc.), antioxidants (e.g. dibutylhydroxytoluene, nordihydroguaiaretic acid, etc.), preservatives (e.g. dehydroacetic acid, etc.), feeding error preventing agents (e.g. red peper powders, etc.), incentive flavor (e.g. cheese flavor, onion flavor, etc.).

The thus obtained formulations may be used as they are or after diluting with water, etc. Alternatively, the formulations may be used as admixture with other insecticides, nematocides, acaricides, bacteriocides, herbicides, plant growth regulators, synergistic agents, fertilizers, soil conditioners, animal feed, etc., or may also be used simultaneously with them, without mixing therewith.

Where the pyridylimidazole derivatives (I) are used as insecticides for agricultural use, the dose is generally 0.1 g to 100 g per 10 ares; when emulsifiable concentrates, wettable powders, flowable concentrates, etc. are used after diluting them with water, the concentration is 0.1 ppm to 500 ppm. Granules, dusts, etc. may be used as they are, without diluting them. For purposes of household and public hygiene, emulsifiable concentrates, wettable powders, flowable concentrates, etc. are diluted with water in a concentration of 0.1 ppm to 500 ppm; oils, aerosol, fumigants, poison baits, etc. may be used as they are.

These doses and concentrations may vary depending upon kind of formulations, timing for application, place applied, method for application, kinds of insect, condition of damages, etc. and may be increased or decreased, irrespective of the ranges set forth above.

Hereafter the present invention is described in more detail, by referring to synthesis examples, formulation examples and test examples but is not deemed to these examples.

Synthesis Example 1 (Synthesis of Compound No. (1))

To a solution of 0.6 g (3 m mol) of 5-methyl-4-pentafluoroethylimidazole in 5 ml of N,N-dimethyl formamide was added slowly 120 mg (3 m mol) of an oily sodium hydride (60%) while cooling with ice, followed by stirring at the same temperature for 10 minutes. After the reaction was completed, to the reaction mixture was added dropwise 0.65 g (3 m mol) of 2,3-dichloro-5-trifluoromethylpyridine, followed by stirring at room temperature for 9 hours. After the reaction was completed, the reaction mixture was poured into water, and extracted with ethyl acetate. Further, then the residue was washed with brine, dried over magnesium sulfate, and concentrated under reduced pressure. The residue was subjected to silica gel chromatography to give 0.5 g of 1-(3-chloro-5-trifluoromethylpyridin-2-yl)-5-methyl-4-pentafluoroethylimidazole.

m.p. 71.0° C.

Synthesis Example 2 (Synthesis of Compound No. (2))

To a solution of 1.0 g (3.8 mol) of 4-(2-bromo-1,1,2,2-tetrafluoroethyl-5-methylimidazole in 5 ml of N,N-dimethyl formamide was added slowly 150 mg (3.8 mol) of an oily sodium hydride (60%) while cooling with ice, followed by stirring at the same temperature for 10 minutes. After the reaction was completed, to the reaction mixture was added dropwise 0.82 g (3.8 m mol) of 2,3-dichloro-5-trifluoromethylpyridine, followed by stirring at room temperature for 9 hours. After the reaction was completed, the reaction mixture was poured into water, and extracted with ethyl acetate. Further, then the residue was washed with brine, dried over magnesium sulfate, and concentrated under reduced pressure. The obtained product was subjected to silica gel chromatography to give 0.8 g of 4-(2-bromo-1,1,2,2-tetrafluoro)ethyl-1-(3-chloro-5-trifluoromethylpyridin-2-yl)-5-methylimidazole.

n $^{22.1}_D$ 1.4829

Synthesis Example 3 (Synthesis of Compound No. (3))

To a solution of 1.0 g (5 m mol) of 5-methyl-4-(1,1,2,2-tetrafluoroethylimidazole in 5 ml of N,N-dimethyl formamide was added slowly 200 mg (5 m mol) of an oily sodium hydride (60%) while cooling with ice, followed by stirring at the same temperature for 10 minutes. After the reaction was completed, to the reaction mixture was added dropwise 1.08 g (5 m mol) of 2,3-dichloro-5-trifluoromethylpyridine, followed by stirring at room temperature for 9 hours. After the reaction was completed, the reacton mixture was poured into water, and extracted with ethyl acetate. Further, then the residue was washed with brine, dried over magnesium sulfate, and concentrated under reduced pressure. The obtained product was subjected to silica gel chromatography to give 0.9 g of 1-(3-chloro-5-trifluoromethylpyridin-2-yl)-5-methyl-4-(1,1,2,2tetrafluoroethyl)imidazole.

n $^{24.5}_D$ 1.4744

Synthesis Example 4 (synthesis of Compound No. (4))

To a solution of 0.50 g (3 m mol) of 5-methyl-4-trifluoromethylimidazole in 5 ml of N,N-dimethyl formamide was added slowly 133 mg (3 m mol) of an oily sodium hydride (60%) while cooling with ice, followed by stirring at the same temperature for 10 minutes. After the reaction was completed, to the reaction mixture was added dropwise 0.62 g (3 m mol) of 2,3-dichloro-5-trifluoromethylpyridine, followed by stirring at room temperature for 8 hours. After the reaction was completed, the reaction mixture was poured into water, and extracted with ethyl acetate. Further, then the residue was washed with brine, dried over magnesium sulfate, and concentrated under reduced pressure. The residue was subjected to silica gel chromatography to give 0.48 g of 1-(3-chloro-5-trifluoromethylpyridin-2-yl)-5-methyl-4-trifluoromethylimidazole.

m.p. 59.4° C.

Synthesis Example 5 (Synthesis of Compound No. (5))

To a solution of 0.6 g (2.4 m mol) of 4-heptafluoropropyl-5-methylimidazole in 5 ml of N,N-dimethyl formamide was added slowly 100 mg (2.4 m mol) of an oily sodium hydride (60%) while cooling with ice, followed by stirring at the same temperature for 10 minutes. After the reaction was completed, to the reaction mixture was added dropwise 0.52 g (2.4 m mol) of 2,3-dichloro-5-trifluoromethylpyridine, followed by stirring at room temperature for 9 hours. After the reaction was completed, the reaction mixture was poured into water, and extracted with ethyl acetate. Further, then the residue was washed with brine, dried over magnesium sulfate, and concentrated under reduced pressure. The obtained product was subjected to silica gel chromatography to give 0.4 g of 1-(3-chloro-5-trifluoromethylpyridin-2-yl)-4-heptafluoropropyl-5-methylimidazole.

m.p. 62.5° C.

Synthesis Example 6 (Synthesis of Compound No. (6))

To a solution of 0.6 g (2 m mol) of 5-methyl-4-nanofluorobutylimidazole in 5 ml of N,N-dimethyl formamide was added slowly 80 mg (2 m mol) of an oily sodium hydride (60%) while cooling with ice, followed by stirring at the same temperature for 10 minutes. After the reaction was completed, to the reaction mixture was added dropwise 0.37 g (2 m mol) of 2,3-dichloro-5-trifluoromethylpyridine, followed by stirring at room temperature for 9 hours. After the reaction was completed, the reaction mixture was poured into water, and extracted with ethyl acetate. Further, then the residue was washed with brine, dried over magnesium sulfate, and concentrated under reduced pressure. The obtained product was subjected to silica gel chromatography to give 0.5 g of 1-(3-chloro-5-trifluoromethylpyridin-2-yl)-5-methyl-4-nanofluoro butylimidazole.

$n^{25.0}_D$ 1.4385

Synthesis Example 7 (Synthesis of Compound No. (7))

To a solution of 0.5 g (2.5 m mol) of 5-methyl-4-pentafluoroethylimidazole in 5 ml of N,N-dimethylformamide is added slowly 100 mg (2.5 m mol) of an oily sodium hydride (60%) while cooling with ice, followed by stirring at the same temperature for 20 minutes. After the reaction is completed, to the reaction mixture is added dropwise 0.62 g (2.5 m mol) of 2-chloro-3,5-bis(-trifluoromethyl)pyridine, followed by stirring at room temperature for 9 hours. After the reaction is completed, the reaction mixture is poured into water, and extracted with ethyl acetate. Further, then the residue is washed with brine, dried over magnesium sulfate and concentrated under reduced pressure. The obtained product is subjected to silica gel chromatography to give 1-[3,5-bis(trifluoro-methyl)pyridine-2-yl]-5-metyl-4-pentafluoro-ethylimidazole.

Synthesis Example 8 (Synthesis of Compound No. (8))

To a solution of 0.5 g (2.5 m mol) of 5-methyl-4-pentafluoroethylimidazole in 5 ml of N,N-dimethyl formamide is added slowly 100 mg (2.5 m mol) of an oily sodium hydride (60%) while cooling with ice, followed by stirring at the same temperature for 20 minutes. After the reaction is completed, to the reaction mixture is added dropwise 0.50 g (2.5 m mol) of 2,3-dichloro-5-difluoromethoxypyridine, followed by stirring at room temperature for 9 hours. After the reaction is completed, the reaction mixture is poured into water, and extracted with ethyl acetate. Further, then the residue is washed with brine, dried over magnesium sulfate, and concentrated under reduced pressure. The obtained product is subjected to silica gel chromatography to give 1-(3-chloro-5-difluoromethoxypyridin-2-yl)-5-methyl-4-pentafluoroethylimidazole.

Synthesis Example 9 (Synthesis of Compound No. (9))

To a solution of 0.5 g (3.6 m mol) of 4-tert-butyl-5-methylimidazole in 5 ml of N,N-dimethyl formamide is added slowly 150 mg (3.7 m mol) of an oily sodium hydride (60%) while cooling with ice, followed by stirring at the same temperature for 20 minutes. After the reaction is completed, to the reaction mixture is added dropwise 0.71 g (3.6 m mol) of 2,3-dichloro-5-trifluoromethylpyridine, followed by stirring at room temperature for 9 hours. After the reaction is completed, the reacton mixture is poured into water, and extracted with ethyl acetate. Further, then the residue is washed with brine, dried over magnesium sulfate, and concentrated under reduced pressure. The obtained product is subjected to silica gel chromatography to give 4-tert-butyl-1-(3-chloro-5-trifluoromethylpyridin-2-yl)-5-methylimidazole.

Next, Formulation examples are shown, wherein parts are all by weight and the compounds of the present invention are designated by the compound numbers shown in Table 1.

Formulation Example 1 (Emulsifiable concentrate)

After 10 parts each of Compounds (1) through (9) are dissolved in 35 parts of xylene and 35 parts of dimethylformamide, 14 parts of polyoxyethylene styrylphenyl ether and 6 parts of calcium dodecylbenzenesulfonate are added to the solutions. The resulting mixtures are thoroughly mixed stirred to give 10% emulsifiable concentrate, respectively.

Formulation Example 2 (Wettable powder)

After 20 parts of Compound (1) through (9) are added to a mixture of 4 parts of sodium laurylsulfate, 2 parts of calcium ligninsulfonate, 20 parts of synthetic hydrated silicon dioxide fine powders and 54 parts of diatomaceous earth, the mixture is mixed and stirred with a juice mixer to give 20% wettable powder.

Formulation Example 3 (Granules)

Five parts of fine powders of synthetic hydrated silica, 5 parts of sodium dodecylbenzene-sulfonate, 30 parts of bentonite and 55 parts of clay are added to 5 parts of each of Compound Nos. (1), (4) and (5), and the resultant mixture is pulverized and kneaded with a suitable amount of water. The mixture is granulated in a granulator and air-dried to give granules containing the active ingredient in 5%.

Formulation Example 4 (Granules)

Five parts of sodium dodecylbenzenesulfonate, 30 parts of benotnite and 60 parts of clay are added to 5 parts of each of Compound Nos. (2), (3) and (6), and the resultant mixture is pulverized and kneaded with a suitable amount of water. The mixture is granulated in a granulator and air-dried to give granules containing the active ingredient in 5%.

Formulation Example 5 (Dust)

After 1 part of Compound (1) through (9) is dissolved in a appropriate amount of acetone, 5 parts of synthetic hydrated silicon dioxide fine powders, 0.3 part of PAP and 93.7 parts of clay are added to the solution. The mixture is mixed and stirred with a juice mixer and acetone is evaporated off to give 1% dust.

Formulation Example 6 (Flowable concentrate)

To 28.5 parts of an aqueous solution containing 2 parts of polyvinyl alcohol, 20 parts of each of Compound Nos. (1), (4) and (5) and 1.5 parts of sorbitan trioleate are added, and the resultant mixture is finely pulverized by the aid a sand grinder to give particles of less than 3 microns in average particle size. To the resultant mixture, 40 parts of an aqueous solution containing 0.05 part of xanthane gum and 0.1 part of aluminum magnesium silicate are added, followed by addition of 10 parts of propylene glycol. The mixture is gently stirred to give a flowable concentrate containing the active ingredient in 20%.

Formulation Example 7 (Flowable concentrate)

To 40 parts of an aqueous solution containing 2 parts of polyvinyl alcohol, 10 parts of each of Compound Nos. (2), (3) and (6) are added, and the resultant mixture is stirred in a mixer. To the thus obtained dispersion, 40 parts of an aqueous solution containing 0.05 part of xanthane gum and 0.1 part of aluminum magnesium silicate are added, followed by addition of 10 parts of propylene glycol. The mixture is genetly stirred to give a flowable concentrate containing the active ingredient in 10%.

Formulation Example 8 (Oil spray)

After 0.1 part of Compound (1) through (9) is dissolved in 5 parts of xylene and 5 parts of trichloroethane, the solution is mixed with 89.9 parts of deodorized kerosene to give 0.1% oil spray.

Formulation Example 9 (Oil-based aerosol)

After 0.1 part of Compound (1) through (9), 0.2 part of tetramethrin, 0.1 part of d-phenothrin, 10 parts of trichloroethane and 59.6 parts of deodorized kerosene are mixed with each other and dissolved. The solution is filled in an aerosol container. After a valve is mounted to the container, 30 parts of propellant (liquefied petroleum gas) are filled under pressure through the valve to give oil-based aerosol.

Formulation Example 10 (Water-based aerosol)

After 0.2 part of Compound (9), 0.2 part of d-allethrin, 0.2 part of d-phenothrin, 5 parts of xylene, 3.4 parts of deodorized kerosene and 1 part of emulsifier [ATMOS 300 (registered trademark, Atlas Chemical Co., Ltd.)] are mixed with each other and dissolved. The solution and 50 parts of distilled water are filled in an aerosol container. After a valve is mounted to the container, 40 parts of propellant (liquefied petroleum gas) are filled under pressure through the valve to give water-based aerosol.

Formulation Example 11 (Mosquito coil)

After 0.3 g of d-allethrin is added to 0.3 g of Compound (1) through (9), the mixture is dissolved in 20 ml of acetone. The solution is then uniformly mixed with 99.4 g of carrier for mosquito-coil (taba powder : sake lees powder: wood powder of 4:3:3) with stirring and 120 ml of water is then added to the mixture. The mixture is thoroughly kneaded, molded and dried to give mosquito-coil.

Formulation Example 12 (Electric mosquito mat)

Acetone is added to 0.4 g of Compound (1) through (9), 0.4 g of d-allethrin and 0.4 g of piperonyl butoxide to dissolve and make the whole volume 10 ml. This solution, 0.5 ml, is uniformly impregnated with a base material for electric mat (a mixture of cotton linter and pulp solidified in a plate-like form) having 2.5×1.5 cm and a thickness of 0.3 cm to give an electric mosquito mat.

Formulation Example 13 (Fumigant)

After 100 mg of Compound (1) through (9) is dissolved in a appropriate amount of acetone, the solution is impregnated with a porous ceramic plate having 4.0 cm×4.0 cm and a thickness of 1.2 cm to give a fumigant.

Formulation Example 14 (Poison bait)

After 10 mg of Compound (1) through (9) is dissolved in a 0.5 ml acetone, the solution is applied to 5 g of the powder of dry animal food. The powder is dried to give a 0.5% poison bait.

The following Test Examples show some of test results which support the controlling effect of the method of the pyridiylimidazole derivatives (I) on insects. The compounds used for comparison are as follows:

TABLE 2

| Compound Symbol | Chemical Structure | Note |
|---|---|---|
| (A) | [structure with $CH_3$, N, $C_4H_9$-tert, $CH_3$, $CH_3$] | Compound described in U.S. Pat. No. 3,868,458 and 3,940,484 |
| (B) | [structure with $CH_3S$, N, $C_4H_9$-tert, $CH_3$, $CH_3$] | Compound described in U.S. Pat. No. 3,996,366 |

Test Example 1 (Insecticidal test on nymphs of brown planthopper)

The emulsifiable concentrate of the test compound prepared according to Formulation Example 1 was diluted with water (corresponding to 500, 5, 0.5 ppm) and a rice plant seedling (length of about 12 cm) was immersed in the dilution for a minute. After air-drying, the rice plant seedling was put in a test tube and about 30 nymphs of brown planthopper (*Nilaparvata lugens*) were released. Six days after, the nymphs were observed if they were alive or dead. Criterion for the judgment is as follows.
a: no insect was alive.
b: alive insects were 5 or less.
c: alive insects were 6 or more.
The results are shown in Table 3.

TABLE 3

| Test Compound | Concentration (ppm) | Mortality |
|---|---|---|
| (1) | 500 | a |
|  | 50 | a |
| (2) | 500 | a |
|  | 50 | a |
| (3) | 500 | a |
|  | 50 | a |
| (4) | 500 | a |
|  | 50 | a |
| (5) | 500 | a |
|  | 50 | a |
| (6) | 500 | a |
| (A) | 500 | c |

TABLE 3-continued

| Test Compound | Concentration (ppm) | Mortality |
| --- | --- | --- |
| (B) | 500 | c |
| no treatment | — | c |

Compound Nos. (1) and (2) also showed "a" at a concentration of 0.5 ppm.

Text Example 2 (Insecticidal test on southern corn rootworm)

On the bottom of a polyethylene cup having a diameter of 5.5 cm, a filter paper which is of the same size was laid down and 1 ml of an aqueous dilution (500 or 50 ppm) of the emulsifiable concentrate of the test compound prepared according to Formulation Example 1 was dropped onto the filter paper and one corn sprout was put as feed. About 30 eggs of southern corn rootworm (*Diabrotica undecimpunctata*) were put in the cup. Eight days after the cup was covered, dead or alive larvae hatched were examined. Criterion for the judgment is as follows.

a: no insect was alive.
b: alive insects were 5 or less.
c: alive insects were 6 more.

As the results, compound Nos. (1), (2), (3) and (4) showed "a" at a concentration of 500 ppm and 50 ppm. On the other hand, no treatment showed "c".

Test Example 3 (Insecticidal test on common mosquito)

The emulsifiable concentrate of the test compound prepared according to Formulation Example 1 was diluted with water and 0.7 ml of the dilution was added to 100 ml of ion exchange water (concentration of the effective ingredient was 3.5 ppm). In the mixture were released 20 last instar larvae of common mosquito (*Culex pipiens pallens*). One day after the release, mortality was examined.

Cirterion for the judgment is as follows.

a: 90% or more
b: not less than 10% but less than 90%
c: less than 10%

As the results, compound Nos. (1), (2), (3), (4), (5) and (6) showed "a" at a concentration of 3.5 ppm. On the other hand, no treatment showed "c".

Test Example 4 (Insecticidal test on German cockroach)

On the bottom of a polyethylene cup having a diameter of 5.5 cm, a filter paper which is of the same size was laid down and 0.7 ml of an aqueous dilution (500 ppm) of the mulsifiable concentrate of the test compound prepared according to Formulation Example 1 was dropped onto the filter paper. As feed, 30 mg of sucrose was uniformly spread thereon. In the cup, 10 adult males of German cockroach (*Blattella germanica*) were released. Six days after the cup was covered, dead or alive insects were examined to determine mortality.

The results are shown in Table 4.

TABLE 4

| Test Compound | Concentration (ppm) | Mortality (%) |
| --- | --- | --- |
| (1) | 500 | 100 |
| (2) | 500 | 100 |
| (3) | 500 | 100 |
| (4) | 500 | 100 |
| (5) | 500 | 100 |
| (A) | 500 | 0 |
| (B) | 500 | 0 |
| no treatment | — | 0 |

Test Example 5 (Insecticidal test on housefly)

On the bottom of a polyethylene cup having a diameter of 5.5 cm, a filter paper which is of the same size was laid down and 0.7 ml of an aqueous dilution (500 ppm) of the emulsifiable concentrate of the test compound prepared according to Formulation Example 1 was dropped onto the filter paper. As feed, 30 mg of sucrose was uniformly spread thereon. In the cup, 10 adult females of housefly (*Musca domestica*) were released. Forty eight hours after the cup was covered, dead or alive insects were examined to determine mortality (2 replications).

As the results, compound Nos. (1), (2), (3), (4) and (5) showed a 100% mortality at a concentration of 500 ppm. On the other hand, no treatment showed a zero percent.

What is claimed is:

1. A pyridylimidazole derivative having the formula:

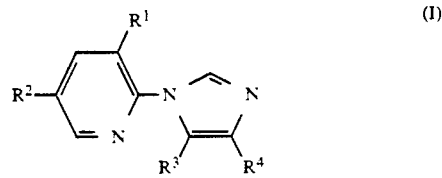

wherein $R^1$ is a halogen atom, a nitro group or a trifluoromethyl group; $R^2$ is a $C_1-C_3$ haloalkyl group or a $C_1-C_3$ haloalkoxy group; $R^3$ is a $C_1-C_3$ alkyl group; $R^4$ is a tert-butyl group or a $C_1-C_4$ haloalkyl group.

2. The pyridylimidazole derivative according to claim 1, wherein $R^1$ is a fluorine atom, a chlorine atom or a nitro group; $R^2$ is a $C_1-C_3$ haloalkyl group which comprises at least a fluorine atom; $R^3$ is a $C_1-C_3$ alkyl group; $R^4$ is a tert-butyl group or a $C_1-C_3$ haloalkyl group which comprises at least a fluorine atom, a chlorine atom or a bromine atom as the halogen atom.

3. The pyridylimidazole derivative according to claim 1, wherein $R^1$ is a fluorine atom or a chlorine atom; $R^2$ is a trifluoromethyl group; $R^3$ is a methyl group; $R^4$ is a $C_1-C_3$ haloalkyl group which comprises at least a fluorine atom, a chlorine atom or a bromine atom as the halogen atom.

4. The pyridylimidazole derivative according to claim 1, wherein $R^1$ is a chlorine atom; $R^2$ is a trifluoromethyl group; $R^3$ is a methyl group; $R^4$ is a haloalkyl group represented by the formula, $-CF_2CF_2X$, in which X is a hydrogen atom, a fluorine atom, a chlorine atom or a bromine atom.

5. The pyridylimidazole derivative according to claim 1, which is 1-(3-chloro-5-trifluoromethyl-pyridine-2-yl)-5-methyl-4-pentafluoroethylimidazole.

6. The pyridylimidazole derivative according to claim 1, which is 4-(2-bromo-1,1,2,2-tetrafluoroethyl)-1-(3-chloro-5-trifluoromethylpyridin-2-yl)-5-methylimidazole.

7. The pyridiylimidazole derivatives according to claim 1, which is 1-(3-chloro-5-trifluoromethyl-pyridin-2-yl)-5-methyl-4-(1,1,2,2-tetrafluoroethyl) imidazole.

8. An insecticidal composition which comprises an insecticidally effective amount of the pyridylimidazole derivative according to claim 1 and an inert carrier.

9. A method for controlling insect pests which comprises applying an insecticidally effective amount of the pyridiylimidazole derivative according to claim 1 to the insect pests or to the locus where insect pests propagate.

* * * * *